United States Patent [19]

Thomas

[11] Patent Number: 5,622,578
[45] Date of Patent: Apr. 22, 1997

[54] METHOD FOR MANUFACTURING REFASTENABLE FASTENING SYSTEMS INCLUDING A FEMALE LOOP FASTENING COMPONENT AND THE PRODUCTS PRODUCED THEREFROM

[75] Inventor: Dennis A. Thomas, Cincinnati, Ohio

[73] Assignee: The Procter & Gamble Company, Cincinnati, Ohio

[21] Appl. No.: 507,106

[22] Filed: Jul. 26, 1995

Related U.S. Application Data

[62] Division of Ser. No. 336,277, Nov. 8, 1994.

[51] Int. Cl.⁶ .................................................. B29C 47/06
[52] U.S. Cl. ..................... 156/66; 156/242; 156/242.11; 264/167; 264/173.1; 264/243; 604/391
[58] Field of Search ................... 156/66, 242, 242.11; 604/391; 24/306, 442, 443, 445, 447, 480; 264/167, 173.1, 243, 331.11

[56] References Cited

U.S. PATENT DOCUMENTS

| | | | |
|---|---|---|---|
| 2,714,750 | 8/1955 | Facciolo. | |
| 3,417,440 | 12/1968 | Billarant | 24/450 X |
| 3,522,637 | 8/1970 | Brumlik | 24/451 X |
| 3,557,407 | 1/1971 | Lemelson. | |
| 3,594,865 | 7/1971 | Erb. | |
| 3,745,587 | 7/1973 | Bradley | 2/114 |
| 4,654,246 | 3/1987 | Provost et al. | 428/88 |
| 4,794,028 | 12/1988 | Fischer | 428/100 |
| 4,872,243 | 10/1989 | Fischer | 24/442 |
| 4,973,326 | 11/1990 | Wood et al. | 24/450 X |
| 4,984,339 | 1/1991 | Provost et al. | 24/452 |
| 5,032,122 | 7/1991 | Noel et al. | 24/442 X |
| 5,058,247 | 10/1991 | Thomas et al. | 24/448 |
| 5,100,400 | 3/1992 | Mody et al. | 604/391 |
| 5,116,563 | 5/1992 | Thomas et al. | 24/442 X |
| 5,131,119 | 7/1992 | Murasaki et al. | 24/452 |
| 5,180,534 | 1/1993 | Thomas et al. | 264/145 |
| 5,230,851 | 7/1993 | Thomas | 24/442 X |
| 5,300,058 | 4/1994 | Goulait et al. | 24/448 X |
| 5,318,741 | 6/1994 | Thomas | 264/519 |
| 5,324,279 | 6/1994 | Lancaster et al. | 24/306 X |
| 5,325,569 | 7/1994 | Goulait et al. | 24/448 |
| 5,326,415 | 7/1994 | Thomas et al. | 156/244.11 |
| 5,326,612 | 7/1994 | Goulait | 24/452 X |
| 5,392,498 | 2/1995 | Goulait et al. | 24/452 |

FOREIGN PATENT DOCUMENTS

| | | |
|---|---|---|
| 0580073A3 | 1/1994 | European Pat. Off.. |
| 56017225 | 2/1981 | Japan. |
| 3215204 | 9/1991 | Japan. |
| 6033359 | 2/1994 | Japan. |
| WO93/00215 | 1/1993 | WIPO. |

*Primary Examiner*—Michael W. Ball
*Assistant Examiner*—Sam Chuan Yao
*Attorney, Agent, or Firm*—Harness, Dickey & Pierce, P.L.C.

[57] ABSTRACT

The invention is a refastenable mechanical fastening system including rows of female loops joined to a substrate. The loops taper from the base to the distal end and are typically nonperpendicularly oriented relative to the plane of the substrate. The shanks of each loop may also have an azimuthal angle relative to the machine direction of the substrate. Each loop includes an opening for receiving a portion of the prong of a male hook component. The loops are manufactured by the process of extruding liquid material through the apertures of a depositing member onto a moving substrate to form the base of the loop, stretching the liquid material in a direction parallel to the plane of the substrate, severing the stretched material to form a distal end which fuses with an adjacent amount of stretched material to form a loop. The advantageous usage of the fastening system in an article of manufacture, such as a disposable absorbent article, and more specifically, a diaper is also disclosed.

10 Claims, 5 Drawing Sheets

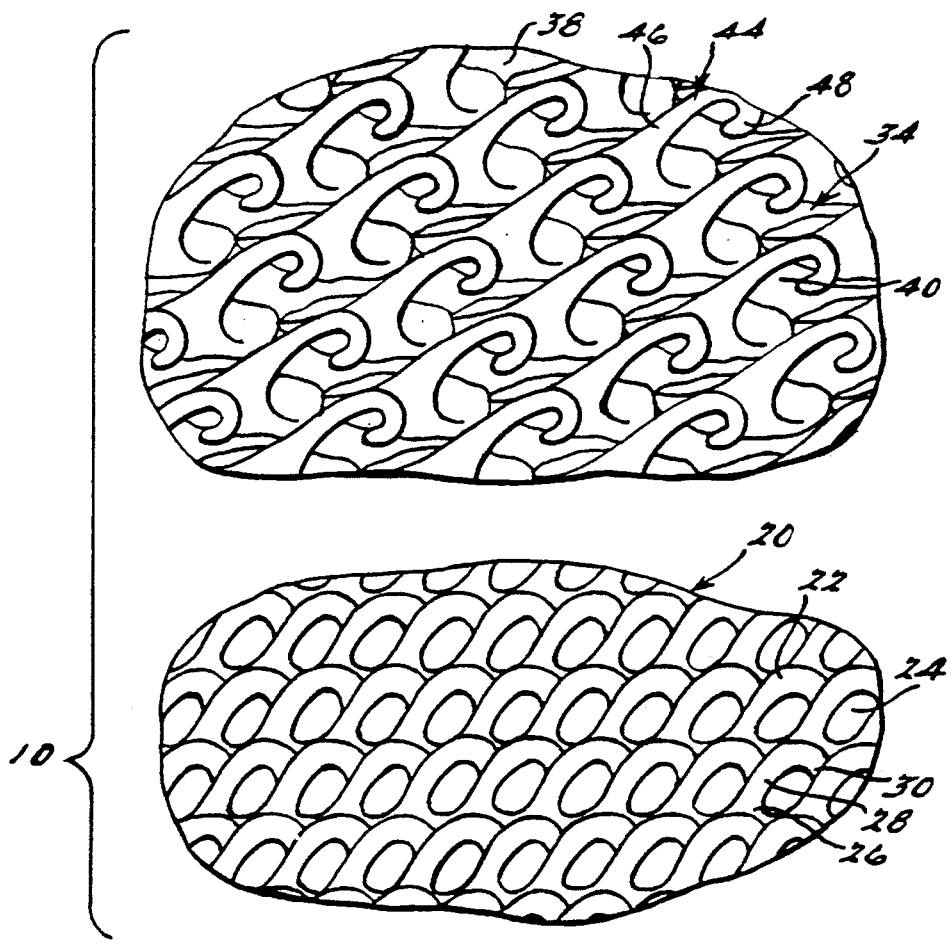
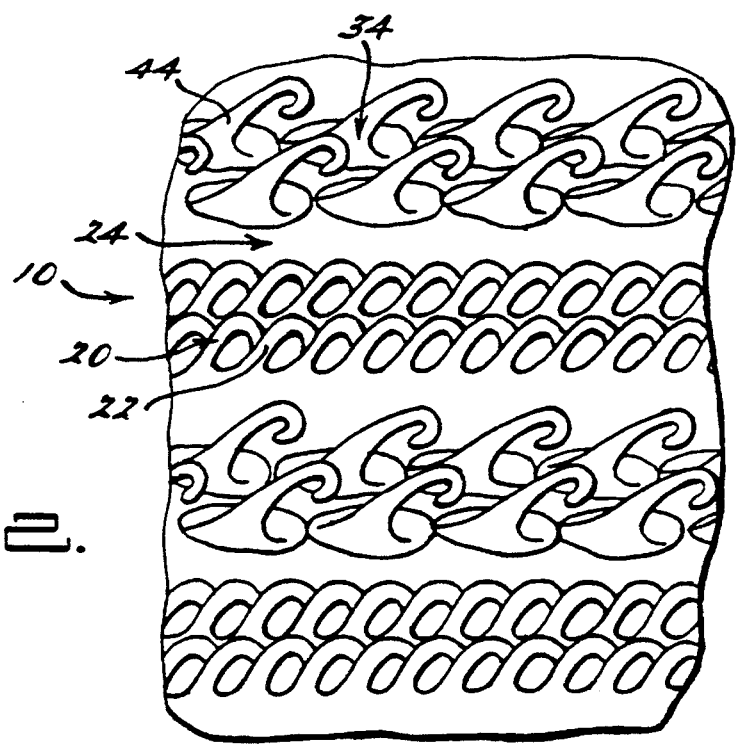

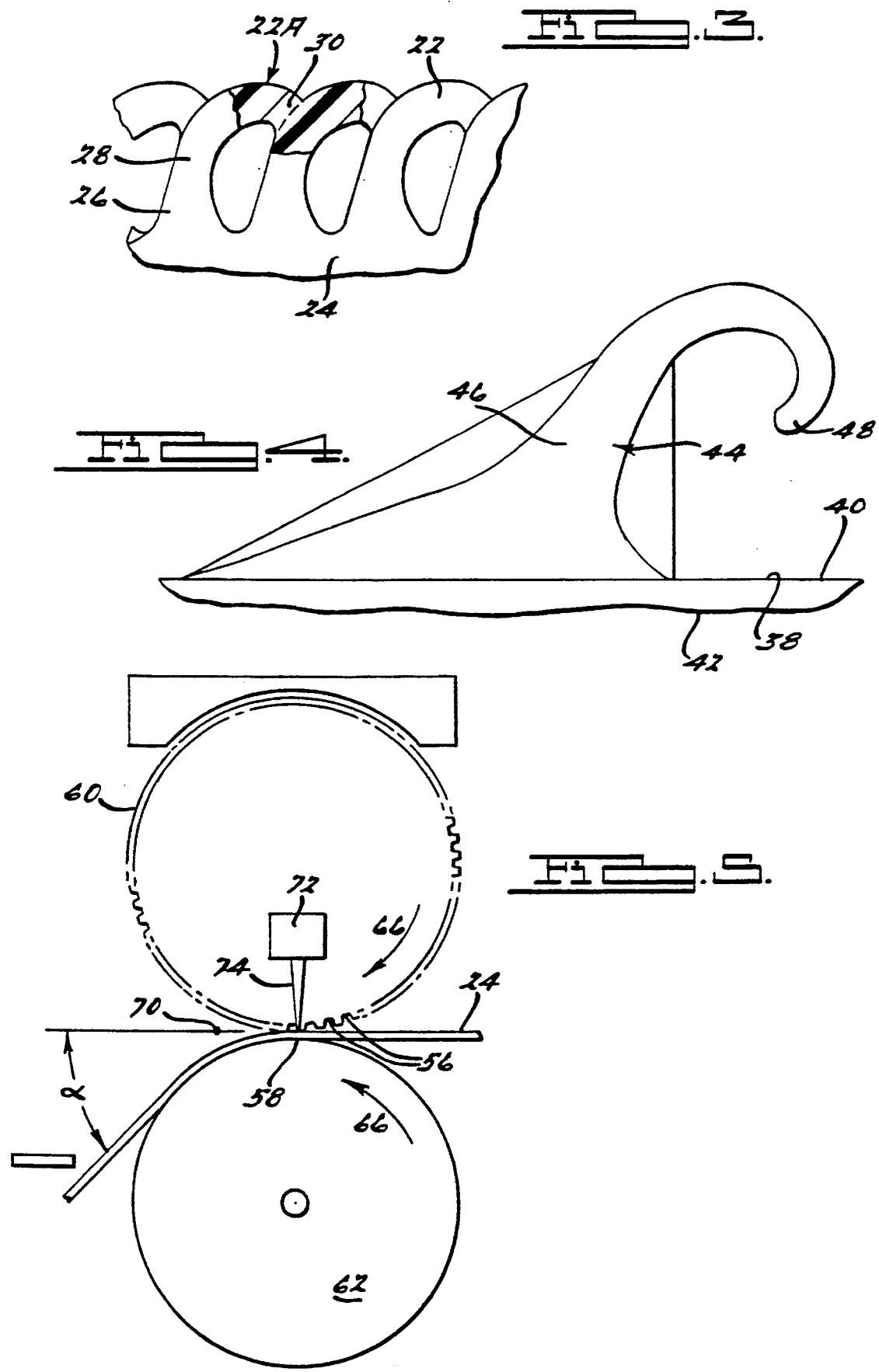

METHOD FOR MANUFACTURING REFASTENABLE FASTENING SYSTEMS INCLUDING A FEMALE LOOP FASTENING COMPONENT AND THE PRODUCTS PRODUCED THEREFROM

This is a division of U.S. patent application Ser. No. 08/336,277, filed Nov. 8, 1994.

FIELD OF THE INVENTION

The present invention relates to refastenable fastening systems comprising a male component and a female component, and relates more particularly to the female component including free formed loops and the process of manufacturing such female components.

BACKGROUND OF THE INVENTION

Refastenable fastening devices of the hook and loop variety are currently widely used. Such refastenable fastening devices have been used in clothing, disposable articles, and various miscellaneous articles such as safety belts and the like. Such devices are used when it is desirable to create a refastenable bond between two or more articles or between several surfaces of the same article. In certain applications, these refastenable fastening devices have replaced conventional buckles, zippers, buttons, snaps, tie fasteners, and sewing.

A popular type of mechanical fastener currently in wide use which utilizes mechanical entanglement to create a refastenable bond is sold under the trademark "VELCRO". VELCRO fastening devices are described in greater detail in U.S. Pat. No. 2,717,437; U.S. Pat. No. 3,009,235; U.S. Pat. No. 3,266,113; U.S. Pat. No. 3,550,837; U.S. Pat. No. 4,169,303; and U.S. Pat. No. 4,984,339; among others.

VELCRO fasteners utilizes two components, a male component and a female component. The male and female components are open referred to as the hook and loop components, respectively. The hook component consists of a fabric which contains a plurality of resilient, upstanding hook-shaped elements. The female component of the fastening device consists of a fabric containing a plurality of upstanding loops on its surface. When the hook component and the loop component are pressed together in a face-to-face relationship to close the fastening device, the hooks entangle the loops forming a plurality of mechanical bonds between the individual hooks and loops. When these bonds have been created, the components will not generally disengage under normal conditions. However, when a gradual peeling force is applied to the components, disengagement can be easily effected. Under a peeling force, since the hooks are comprised of a resilient material, they will readily open to release the loops.

While the VELCRO type of fastening devices have been found to be relatively useful on disposable diapers, disposable packages, cartons and the like, the use of such fastening devices on disposable articles has been limited due to the fact that such fastening devices are relatively costly to manufacture. The high manufacturing costs are typically associated with both the hook and the loop components of these devices.

Conventional hook and loop components of the VELCRO variety are typically formed by making a fabric with a number of woven loops extending outwardly from a backing. The loops may be provided by weaving a base fabric containing supplementary threads to form the loops, or by knitting loops into a fabric. In other hook and loop components, the loops may be formed by pleating or corrugating processes, where the loops are subsequently cut to form the hook components.

These processes generally produce costly hook and loop fastening materials because they are relatively stow. The hook and loop components of such fastening devices are also usually made out of the same relatively expensive material. This material is generally relatively expensive for the hook component because the material used in the hook component needs to be resilient so that the hooks can disengage from the loop component when the device is opened. Additionally, the material is generally relatively expensive due to the need of such material to be strong enough to hold the engaged hooks when subjected to forces applied on the fastening device.

Several attempts have been made to make alternative types of female components for fastening devices. However, such attempts have generally suffered from a number of drawbacks.

One such attempt is described in U.S. Pat. No. 3,708,833 issued to Ribich, et al. on Jan. 9, 1973. The Ribich, et al. patent discloses a refastenable fastening device having a female component that comprises reticulated urethane foam secured to a backing layer. The female component disclosed in the Ribich, et al. patent suffers from the drawback that foams typically do not have enough openings for the hooks of conventional hook components to penetrate. Reticulated foam also does not have sufficient strength to hold such hooks when forces are applied to the fastening device. Further, manufacturing reticulated foam is a relatively expensive process.

U.S. Pat. No. 3,905,071 issued to Brumlik on Sep. 16, 1975 discloses a "press-through self-gripping device." The device described in the Brumlik patent does not appear to be suitable for use in a refastenable fastening device that utilizes a conventional mating hook component with resilient hooks. The fastening device disclosed in the Brumlik patent is intended to be used for fastening one or more sheets of material between a gripping member and a receiving member. The gripping member disclosed in the Brumlik patent has rigid and stiff needled shaped elements for gripping elements. These needle-like elements are particularly unsuitable for use in fastening devices on disposable absorbent articles. The disclosure of the Brumlik patent, thus, appears to be limited to the devices that employ gripping elements adapted to penetrate and pass through several sheets of material and lodge inside a receiving member.

Therefore, there is a need for a low cost fastening deuce for disposable articles. In particular, there is a need for such low cost fastening devices to perform in a manner comparable to the more expense commercially-available fastening devices.

It is an object of the present invention to provide an improved low-cost female component for a fastening devices.

It is another object of the present invention to provide a female component for a fastening device that can be used with both commercially-available hook components having resilient individual hooks, as well as led expensive hook components with more brittle hooks than those currently in use.

It is further object of the present invention to provide a low-cost female component that makes more efficient use of materials than existing fastening devices and that utilizes reduced amounts of expensive materials.

It is still another object of the present invention to forth a low cost female component for a refastenable fastening device by stacking materials on top of one another which have certain desired individual characteristics for entangling and engaging the hooks of a mating hook component.

It is a still further object of the present invention to provide a low-cost and improved method for producing such a female component.

These and other objects of the present invention will be more readily apparent when considered in reference to the following description and when taken in connection with the accompanying drawings.

SUMMARY OF THE INVENTION

The invention comprises a fastening system for attachment to a complimentary receiving surface. The fastening system includes a female component having a substrate and a plurality of loops formed by fusing a number of members comprising a base, shank and distal end portion. The base of the prong is joined to the substrate and the shank is contiguous with and project outwardly from the base. The distal end portion is joined to the shank and projects substantially laterally beyond the periphery of the shank. The shank is generally nonperpendicularly oriented relative to the plane of the substrate. The shank has a leading edge and a trailing edge defining a leading angle and trailing angle which are substantially different from each other, so that the sides of the shank are nonparallel. Optionally, the fastening system may include a male component including a plurality of hooks and a female component including a plurality of loops extending from a single substrate, wherein the hooks are essentially nonfused members sometimes referred to in the industry as prongs.

The fastening system may be made according to the process comprising the steps of heating a thermally sensitive material sufficiently to reduce its viscosity for processing, and preferably to at least its melting point, and applying the material in discrete amounts to a substrate through apertures disposed in a predetermined configuration depending upon the desired loop arrangement. The substrate to which the material is to be joined is transported in a first direction relative to the means for depositing the material and the material is deposited on the transported substrate. Once deposited, the material is stretched in a direction having a component generally parallel to the plane of the substrate and the stretched material is severed to form a distal end. The means for depositing the material and corresponding means including the apertures through which the thermally sensitive material is disposed are run at a relatively high rate of speed to cause the distal ends of the prongs to land on an adjacent member or upon itself as desired resulting in the intended loop configuration as will be described in greater detail below.

An illustrative and suitable use for the fastening systems produced by the process of the present invention is in conjunction with a disposable absorbent article, such as a diaper. This nonlimiting example of usage of the present invention is also more fully described below.

BRIEF DESCRIPTION OF THE DRAWINGS

While the specification concludes with claims particularly pointing out and distinctly claiming the subject matter which is regarded as forming the present invention, it is believed that the invention mu be better understood from the following description taken in conjunction with the accompanying drawings in which:

FIG. 1 is a perspective view of the fastening system of the present invention including a female component containing a plurality of loops and a male component containing a plurality of male hooks;

FIG. 2 Is a perspective view of the fastening system of the present invention including the male component and female component disposed on the same substrate;

FIG. 3 is a side elevation view of an array of female loops of the present invention, FIG. 4 is a side elevation view of a male prong of the present invention;

FIG. 5 is a side elevation view of one apparatus which can be used to produce the fastening systems of the present invention;

DETAILED DESCRIPTION OF THE INVENTION

Figure 6:
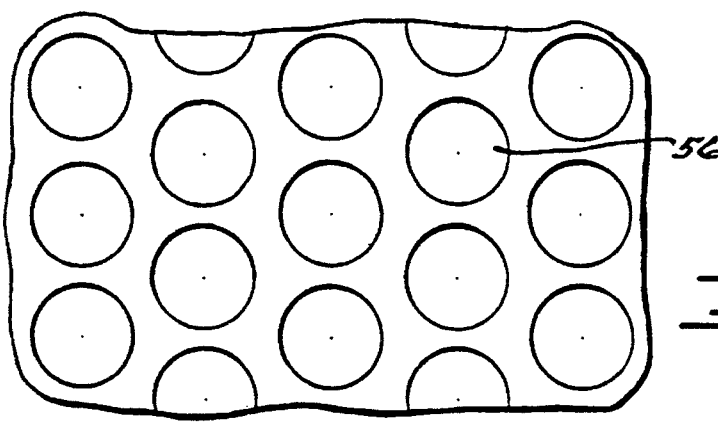
FIG. 6 is a view demonstrating the alternating orientation of the apertures for forming loops contained on the print cylinder apparatus of FIG 5.

1. Overall Characteristics of the Refastenable Fastening System

A preferred embodiment of the refastenable fastening system of the present invention is shown in FIG. 1. The fastening system 10 comprises a female component 20 and complimentary male component 34.

The male portion of the device, hook fastening components (or simply "hook components") 34 otherwise known in the industry as a prong comprise a base 36, such as a fabric 38 that has a first surface 40 and a second surface 42 (as shown in FIG. 4). The fabric 36 contains a plurality of outstanding engaging elements or "hooks" 44 extending from the first surface 40. The hooks 44 have heads 48 disposed on the top of the shanks or stems 46 that extend from the first surface. Particularly preferred hook fastening materials and methods of making such hook fastening materials are disclosed in U.S. Pat. Nos. 5,326,415 which issued Jul. 5, 1994, to Dennis A. Thomas, et al.; 5,318,741 which issued Jun. 7, 1994, to Dennis A. Thomas: 5,230,851 which issued Jul. 27, 1993, to Dennis A. Thomas; 5,058,247 which issued Oct. 22, 1991, to Dennis A. Thomas and 5,116,567 which issued May 26, 1992, to Dennis A. Thomas, all of which have been commonly assigned to The Proctor & Gamble Company of Cincinnati, Ohio, and which patents are incorporated herein by reference.

The female portion 20 of the fastening system 10 includes a plurality of free formed loop components (or simply "look components" or "female components") 22 which receive and are engaged by the hooks 44 of the hook component 32. The female component 22 shown in FIG. 1 composes an array of free formed loops 22, joined to a substrate 24 in a pre-determined pattern.

As illustrated with particular reference to FIG. 3, the loops 22 have a base 26, shank 28 and distal end 30 which blends into another base or shank. The bases 26 of the loops 22A contact and adhere to the substrate 24, and support the proximal ends of the shanks 28.

The shanks 28 project outwardly from the substrate 24 and bases 26 in an arcuate manner. The shanks 28 terminate at a distal end 30. The arcuate projection of the shank 28 allows the distal end 30 to contact and be joined to one or more adjacent loops 22 or to fuse with itself to thereby form an opening or openings 32 for receiving the heads 48 of the hooks 44 as will be described in greater detail below.

The array of loops 22 is produced by methods which yield free formed members 22A as described and claimed hereinbelow. As used herein, the term "free formed" means a structure which is formed from a material deposited onto a substrate and which is not removed from a mold cavity or extrusion die in solid form or with a defined shape. The free formed members 22A are deposited onto a substrate 24 which will be discussed in detail hereinbelow, in a molten, preferably liquid stats and solidify, become fused with another adjacent free formed member 22A or book upon itself, and upon cooling, becomes rigid to have the desired structure and shape as described hereinafter.

The free formed array of loops 22 is preferably produced by a manufacturing process which is simple to a process commonly known as rotary screen printing. This process uses a depositing member in the form of a generally cylindrical screen, referred to herein as the print cylinder 60. Using this process, a substrate 24 having opposed surfaces is passed between the nip 58 of the print cylinder 60 and a backing roll 62, as illustrated at FIG. 5. The print cylinder 60 and backing roll 62 have generally parallel centerline and are maintained in contacting relationship with the substrate 24 as it passes through the nip 58. The depositing member, presently referred to as the print cylinder 60, has an array of perforations, as shown more clearly in FIG. 6, referred to as apertures 56. While the array of perforations or apertures 56 may have differing orientations, it has been found that arranging them in linear offset rows as shown in FIG. 6 results in a maximum number of closed loops 22 being formed per unit area.

The second roll, referred to as the backing roll 62, provides the reaction against the print cylinder 60 to position the substrate 24 against the print cylinder 60 as the substrate 24 passes through the nip 58. Liquid, thermally sensitive material, preferably thermoplastic material, from which the loops Z are eventually formed is supplied from a heated source, such as a heated pressure bar 72. The thermally sensitive material is forced into the apertures 56 by a doctor blade 74 as the print cylinder 60 is rotated about its centerline. The thermally sensitive material is then extruded from the apertures 56 onto the substrate 24 in the desired pattern.

As relative displacement between the substrate 24 and print cylinder 60 increases, the material forming the members 22A, which eventually form the loops 22, is stretched in a direction having a lateral vector component, generally parallel to the plane of the substrate 24, forming the shank 28 and the distal ends 30. Finally, the mail of the material which forms the loop in severed from the distal end 30 by severing means 70. Due to the viscoelastic properties of the thermoplastic, the material retracts and the engaging means 30 contacts the adjacent loop material as shown in FIG. 3 to form the array of loops 22. It is also believed that the loop material retracts under the influences of gravity and shrinkage which occur during coolant. Once the material in the form of member 22A fuses with an adjacent member 22A or back upon itself, material then cools, and preferably freezes, into a solid loop structure 22 having us orifice or opening 32 capable of receiving a male, hook component. The openings 32 allow for entry of the hook. 44 of the hook component into the plans of the female component 20, while the shanks 28 of the loops 22 prevent withdrawal or release of the hooks 44 until desired by the user, or either the peel or shear strength of the female component 20 is otherwise exceeded.

Referring to FIG. 3 to examine the make up of the female component 20 in more detail, the substrate 24 of the fastening system 20 should be strong enough to preclude tearing and separation between individual loops 22 of the female component 20, be a surface to which the loops 22 will readily adhere and be capable of being joined to an article to be secured as desired by a user. As used herein the term joint refers to the condition where a first member, or component, is affixed, or connected to a second member or component, either directly, or indirectly, where the first member or component is affixed or connected to an intermediate member, or component which in turn is affixed, or connected, to the second member or component. The association between the first member, or component, and the second member, or component, is preferably intended to remain for the life of the article. The "substrate" is any exposed surface to which one or more loops 22 are joined.

The substrate 24 should also be capable of being rolled, to support conventional manufacturing processes, and flexible so that the substrate 24 may be bent or flexed in a desired configuration. However, more rigid structures such as cardboard or the like may also be used. The substrate 24 should also be able to withstand the heat of the liquid material which forms the loops 22 being deposited thereon without melting or incurring deleterious effects until such loops 22 freeze. However, the backing roll 62 may be chilled, allowing the process to accommodate substrates 24 which otherwise would not be able to withstand the heat of the liquid loops 22. The substrate 24 should also be available in a variety of widths. Suitable substrates 24 include knitted fabric, woven materials, nonwoven materials, rubber, vinyl and films, including polyolefinic films particularly and preferably polyester films. A polyester film substrate 24 having a basis weight of 17.1 grams per square meter (14.26 grams per square yard) and a thickness of about 0.008 to about 0.15 millimeters (0.0003 to 0.006 inches) has been found suitable. Such materials are commercially available from Hoechst Celanese of Greer, S.C., 29651 and sold under the trade name Hostaphan 2400 polyester film.

The base 26 is the generally planar portion of the loop 22 which is attached to the substrate 24 and is continuous with the proximal end of the shank 28 of the loop. As used herein, the term "base" refers to that portion of me loop 22 which is initially in direct contact with the substrate 24 and supports the shank 28 of the loop 22. It is not necessary that a demarcation be apparent between the base 26 and the shank 28. It is preferred that the shank 28 not separate from the base 26 and that the base 26 not separate from the substrate 24 during use.

The shape of the footprint of the base 26 on the substrate 24 generally corresponds to the shape of the aperture's sectional area at the surface of the print cylinder 60. As used herein, the term "footprint" refers to the planar contact area of the base 26 on the substrate 24. As the aspect ratio of the sides of the footprint increases, the loop 22 may become unstable when subjected to forces, such as gravitational forces, parallel to the shorter dimension of the footprint.

For the embodiments described herein, a base 26 having a footprint of generally circular shape and approximately 0.10 millimeters to 0.30 millimeters (0.004 to 0.012 inches) in diameter is suitable. If it is desired to make the female component 20 have a greater peel or shear strength in a particular direction, the cross sectional area of the base 26 may be modified to amplify such direction, so that the strength and structure integrity relative to the axis parallel to such direction increases. This modification causes the loop 22 to be stronger when pulled in the amplified direction of the base 26.

Figure 7:
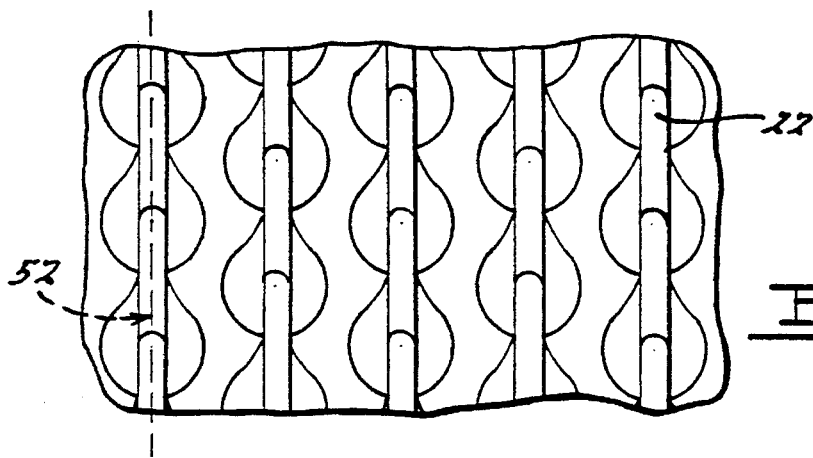
FIG. 7 is a top view illustrating the orientation of offset rows of female loops formed in line.
Figure 8:
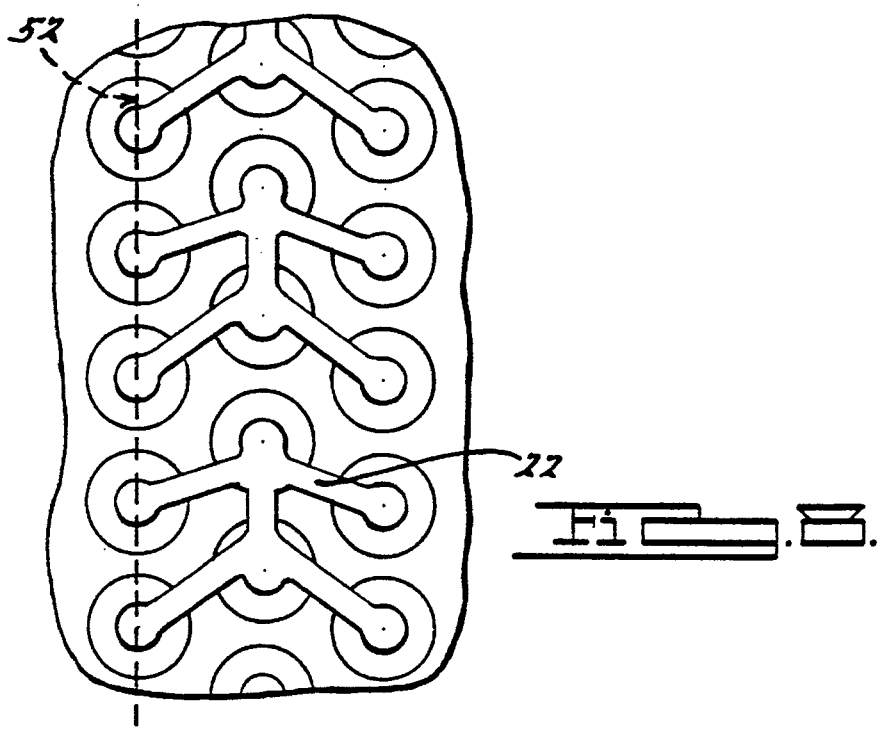
FIG. 8 is a top view illustrating a row of agglomerated loops.
Figure 9:
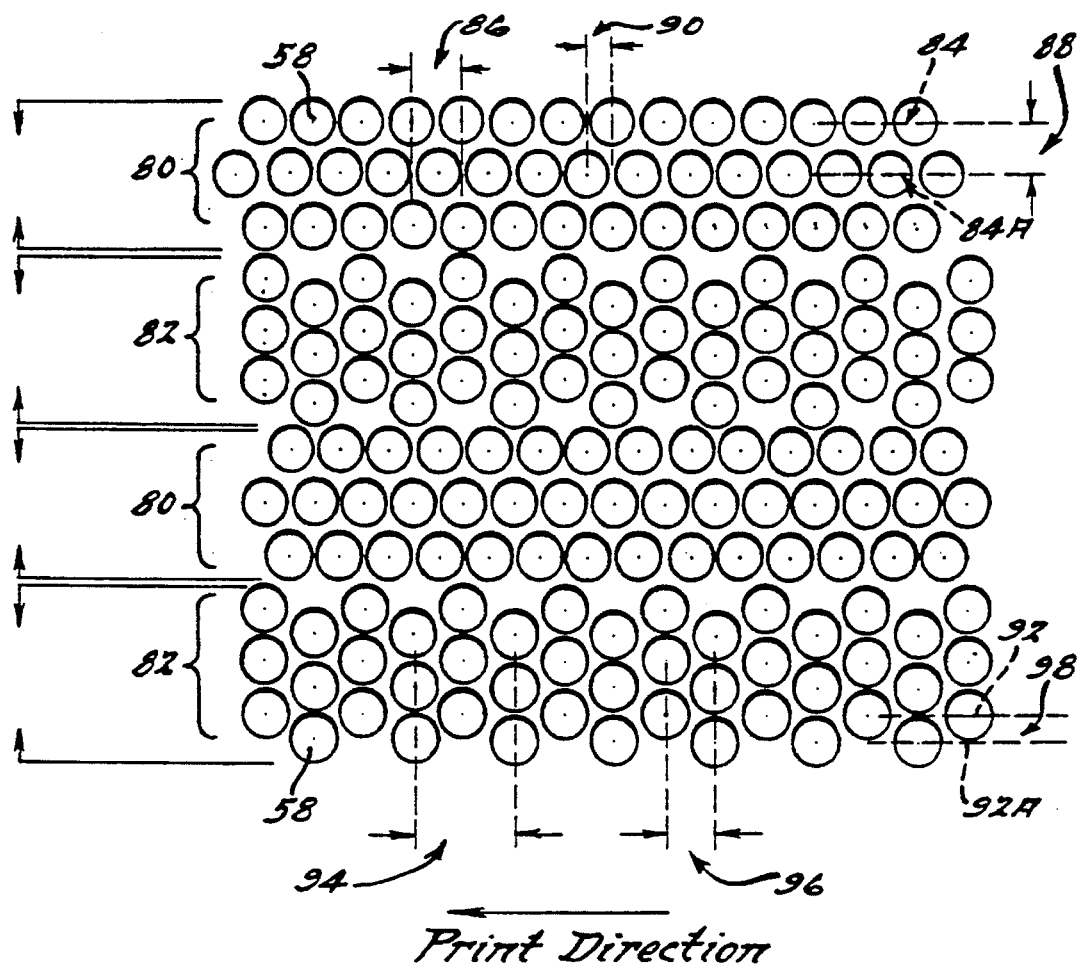
FIG. 9 is a view demonstrating the alternating orientation of apertures for forming both hooks and loops on a single substrate contained on the print cylinder apparatus of FIG. 5.
Figure 10A:
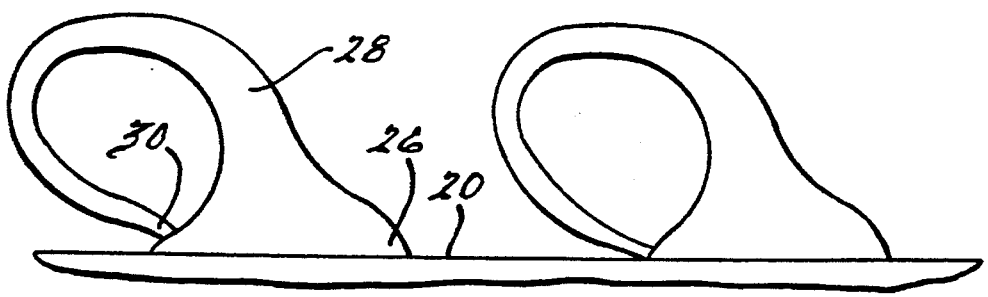
FIG. 10A is a side elevation view illustrating a second row of self included loops.
Figure 10:
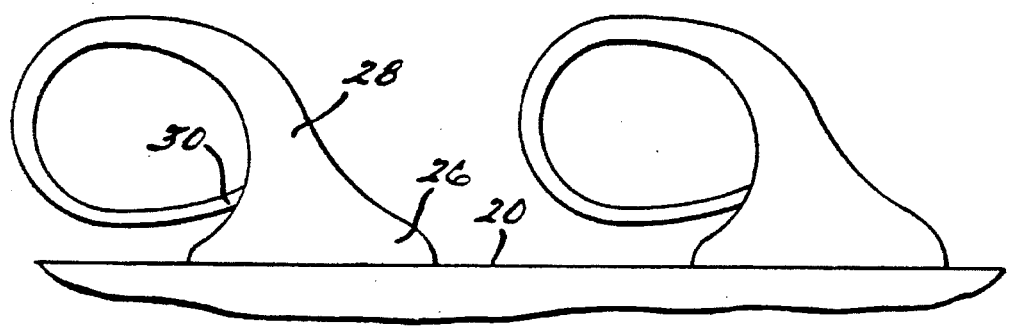
FIG. 10 is a side elevation view illustrating a row of see included loops.

The shank 28 is contiguous with the base 26 and projects outwardly from the base 26 and subs 24. As used herein, the term "shank" refers to that portion of the loop 22 which is intermediate of and contiguous with the base 26 and the distal end 30. The distal end 30 is joined to the shank 28 along one end and affixed to an adjacent loop as shown in FIGS. 7, 8 and 9 or to the shank of the same loop 22 along a second end as shown in FIG. 10.

The array of loops 22 may be of various patterns and densities as desired, to achieve the peel and shear strengths required for the particular application of the fastening system 10. The individual loops 22 should not be so closely spaced as to interfere with and prevent the hooks 44 of the male component 34 from intercepting the shanks 28 of the female component 20. Conversely, the loops 22 should not be so distantly spaced as to require an excessive area of substrate 24 to provide a fastening system of adequate shear and peel strengths.

It is advantageous to dispose the loops 22 in rows, 52 so that each loop 22 is generally equally spaced from an adjacent loop 22. The rows 52 are generally oriented in the machine direction and cross-machine direction according to the manufacturing process described. Generally, each machine direction and cross machine direction row of loops 22 should be substantially equidistantly spaced from the adjacent machine direction and cross machine direction rows of loops 22, to provide a generally uniform stress field throughout the female component 20 and the male component 34 when separation forces are applied to the female component 20 and the male component 34.

As used herein the term "pitch" refers to the distance, measured either in the machine direction or cross-machine direction, between the centers of the footprints of the bases 26 of loops 22 in adjacent rows. Typically a female component 20 having an array of loops 22 with a pitch ranging from about 1.0 millimeters to about 2.0 millimeters (0.039 to 0.078 inches) in both directions is suitable, with a pitch of about 0.64 millimeters (0.025 inches) being preferred. Adjacent machine direction rows are preferably offset approximately one-half pitch in the machine direction to double the distance in the cross direction between the adjacent machine direction rows. This concept is illustrated in FIG. 6.

The loops 22 may be thought of as disposed in a matrix on a one square centimeter grid having an array of loops 22 with about 2 to about 20 rows of loops 22 per centimeter (5 to 50 rows per inch) in both the machine and cross-machine directions. However, when a fastening system 10 having loops 22 is used as the fastening means for a disposable diaper or incontinence brief as described more fully below or is used on a sanitary napkin as a means for securing the sanitary napkin to the panty of the wearer, it is desirable to have a fastening system that is "skin friendly." As used herein the term "skin friendly" refers to a fastening system which is substantially non-irritating and non-abrasive to human skin. It has been found that a fastening system having an array of loops 22 with about 8 to about 40 rows of loops per centimeter (20 to 100 rows per inch) in each direction will produce a fastening system 10 which is substantially non-irritating and non-abrasive to human-skin. This grid will result in a fastening system having about 64 to about 1600 prongs per square centimeter (400 to 10,000 prongs per square inch) of substrate 24.

The method of the present invention can produce a female component having a denser array of loops than can be produced by the methods of the prior art. This is because the density of the array of loops of the present invention is essentially limited only by the number of meshes or apertures that can be produced in the depositing member. Currently, it is possible to produce a depositing member having up to about 1600 meshes per square centimeter (10,000 meshes per square inch). Therefore, it is believed that a female component having up to about 1600 loops per square centimeter (10,000 loops per square inch) can be produced using the method of the present invention.

Preferably, the fastening system 10 will have from about 64 to 1600 loops per square centimeter (400 to 10,000 loops per square inch) of substrate 24. More preferably, the female component 20 will have from about 10 to about 30 rows of loops per centimeter (25 to 75 rows per inch). This grid will result in a female component having from about 100 to about 900 loops per square centimeter (625 to 5625 loops per square inch) of substrate. Most preferably, the female component 20 will have from about 12 to about 24 rows of loops per centimeter (30 to 60 rows per inch). This grid will result in a female component having from about 144 to about 576 loops per square centimeter (900 to 3600 loops per square inch) of substrate. In a preferred embodiment, the female component will have about 16 rows of loops per centimeter (40 rows per inch) in each direction. This grid will result in a female component having about 256 loops per square centimeter.

The loops 22 may be made of any thermally sensitive material which is stable and shape retaining when solid, but not so brittle that failure occurs when the female component 20 is subjected to separation forces. As used herein, "thermally sensitive" means a material which gradually changes from the solid state to the liquid state upon the application of heat. Failure is considered to have occurred when the loops 22 has fractured or can no longer sustain a reaction in the presence of and when subjected to separation forces. Preferably the material has elastic tensile modules, measured according to ASTM Standard D-638, of about 24,600,000 to about 31,600,000 kilograms per square meter (35,000 to 45,000 pounds per square inch).

Further, the loop material should have a melting point low enough to provide for easy processing and a relatively high viscosity to provide a tacky and tough consistency at temperatures near the material melting point, so that the shanks 28 may be stretched and the loops 22 may be easily formed according to the method of manufacture recited below. It is also important that the loops 22 be viscoelastic, to allow for more variation in the parameters affecting loop structure. Material having a complex viscosity ranging from about 20 to about 100 Pascal seconds at the temperature of application to the substrate 24 is suitable.

The viscosity may be measured with a Rheometrics Model 800 Mechanical Spectrometer using the dynamic operating mode at 10 Hertz sampling frequency and 10% material strain. A disk and plate type geometry is preferred, particularly with a disk having a radius of about 12.5 millimeters and a gap of about 1.0 millimeter between the disk and plate.

The loops 22 are preferentially comprised of a thermoplastic material. The term "thermoplastic" refers to uncrosslinked polymers of a thermally sensitive material which flows under the application of heat or pressure. Hot melt adhesive thermoplastics are particularly well suited to manufacture the female component 20 of the present invention, particularly in accordance with the process described and claimed below. As used herein the phrase "hot melt adhesive" refers to thermoplastic compounds, normally solid at room temperature, which become fluid at elevated temperatures and which are applied in the molten state. Examples of hot melt adhesives may be found in the "Handbook Of Adhesives", Second Edition by Irving Skeist, published in 1977 by Van Nostrand Reinhold Company, 135 West 50th Street, New York, N.Y., 10020, which is incorporated herein by reference. Polyester and polyamide hot melt adhesives are particularly suitable and preferred. As used herein, the terms "polyester" and "polyamide" mean chains having repeating ester and amide units respectively.

If a polyester hot melt adhesive is selected, an adhesive having a complex viscosity of about 23±2 Pascal seconds at about 194° C. has been found to work well. If a polyamide hot melt adhesive is selected, an adhesive having a complex viscosity of about 90±10 Pascal seconds at about 204° C. has been found to work well. A polyester hot melt adhesive marketed by the Bostik Company of Middleton, Mass. as No. 7199 has been found to work well.

PROCESS OF MANUFACTURE

FIG. 5 is a side elevational, schematic view of a particularly preferred apparatus used to produce loops according to the method of the present invention. FIG. 5 shows a backing roll 62 and print cylinder 60 which form a nip 58 through which the substrate 24 passes. As the print cylinder 60 and backing roll 62 rotate about their axes, the molten loop material which is extruded through the apertures 56 of the print cylinder 60 onto the moving substrate 24, is stretched in a direction having a vector component parallel to the plane of the substrate 24 and is severed by the means for severing 70 to produce loops having a distal end 30 joined to the shank of an adjacent loop or to itself as will be described in greater detail below. As used herein the term "extrude" refers to forcing a substance through an aperture causing the substance to be shaped, at least partially, by the aperture.

The print cylinder 60 is an example of a particularly preferred depositing member which may be used with the method of the present invention. The depositing member should be made of metal or any other suitable material which can accommodate the temperatures of the molten loop material, provide substantially uniform pitch between the loops 22 in both the machine direction and cross-machine direction, and yield the desired density of loops 22 within the array.

As used herein the phrase "depositing member" refers to anything through which liquid loop material is extruded in dosages corresponding to individual loops 22. The depositing member will generally be a smooth and relatively thin piece of metal or other material having perforations or apertures 56 through which the molten loop material is extruded onto the substrate. The depositing member may be a flat bed screen, a belt screen (such as a continuous band, belt, or conveyor having apertures) or a rotary screen, such as the screens used in the screen printing art. The depositing member, however, may also be in the form of a porous or sintered roll having an internal reservoir continuously pressure fed with molten loop material which is then extruded through the pores of the roll onto the moving substrate. As used herein the term "deposit" means to transfer loop material from the bulk form and dose such material onto the substrate 24 in units corresponding to the members 22A which form the loop 22.

Preferably, the depositing member will be a rotary screen or print cylinder 60. A particularly preferred print cylinder 60 will be a metal cylinder, preferably constructed of nickel, having apertures 56 produced by any means well known in the art and preferably produced by means of photoengraving. Preferably, a circular frame will be mounted on each end of the cylinder, which will provide the screen with structural support, maintain the screen's cylindrical shape, and will also provide a means of holding the screen in position and rotating the screen about its axis without interfering with the blade assembly 74. For convenience of description, the depositing member of the present invention shall be described as a print cylinder 60. It is to be understood, however, that the present invention applies to any method of extruding molten loop material onto a substrate to produce a female component having free-formed loops.

The print cylinder 60 and backing roll 62 may be driven by any means well known in the art such as an external motive force (not shown), or the backing roll 62 may be driven by an external motive force and the print cylinder 60 driven by frictional engagement with the backing roll 62, or vice-versa. Rotary screen printing apparatus which can be modified for use with the method of the present invention are commercially available from Graco/LTI Corporation, P.O. Box 1828, Monteray, Calif. 93940, such as the Graco/LTI Micro-Print hot melt adhesive applicator.

The size, shape and pattern of the apertures 56 in the print cylinder 60 may vary according to the size and shape of the loops and the density of loops 22 in the array that is required for the particular female component desired. The cross sectional area of the aperture 56, taken at the outer surface of the print cylinder 60, generally corresponds with the shape of the footprint of the base 26 of the loop 22. The cross section of the aperture 56 should be approximately equal to the desired cross section of the base 26.

To produce the loop embodiments described herein, a generally cylindrically shaped aperture 56 is adequate. If desired, however, the aperture 56 may be somewhat frusto-conically tapered in shape, having a larger cross section either at the outer surface of the cylinder 60 or inner surface of the cylinder 60. For the print cylinder embodiment described herein an aperture 56 having a diameter or about 0.15 millimeters to about 2.0 millimeters (0.006 to 0.079 inches) produces a suitable loop 22.

There are different methods and apparatus that are suitable to supply molten loop material to the print cylinder 60 and which are well known in the art. One suitable apparatus is disclosed is U.S. Pat. No. 4,876,982, issued Oct. 31, 1989 to Claasen, which is incorporated herein by reference. Another particularly preferred apparatus is the heated pressure bar 72 shown in FIG. 5. The heated pressure bar 72 is disposed within the print cylinder 60 and is substantially parallel to the print cylinder 60. The heated pressure bar 72 has an internal reservoir (not shown) which is fed with liquid loop material and one or more discharge ports (not shown) from which the liquid loop material uniformly flows to the inside surface 76 of the print cylinder 60. Attached to the heated pressure bar 72 is a doctor blade assembly 74. As the print cylinder 60 rotates the doctor blade assembly 74 squeegees the molten loop material along the inner surface 76 of the printed cylinder 60 and forces the liquid loop material into the apertures 56. The doctor blade assembly 74 not only serves to force the molten loop material through the apertures 56, but also provides support to the print cylinder 60 at the point of the nip 58 to prevent the print cylinder 60 from buckling or deforming as it is pressed against the backing roll 62. The backing roll 62 may be constructed of metal or any other suitable material. A backing roll 62 having a rubber coating with a Shore A durometer hardness of about 40 to about 60 may also be used. Preferably, the doctor blade assembly 74 is pressed against the print cylinder 60 with a force of about 80 pounds per square inch as the substrate 24 passes through the nip 58. A suitable heated pressure bar 72 and doctor blade assembly 74 are commercially available from Graco/LTI Corporation, P.O. Box 1828, Monteray, Calif. 93940.

The internal reservoir of the heated pressure bar 72 should have a steady supply of thermally sensitive material. This may be provided by any means well known in the screen printing or hot melt adhesives art, but a particularly preferred method of supplying the heated pressure bar comprises a heated hose assembly (not shown), a heated tank (not shown), and a gear pump (not shown). The gear pump may be driven by a variable speed DC motor (not shown) and should provide constant uniform output at the discharge port of the heated pressure bar 72 at all line speeds. The heated tank, heated hose assembly, and heated pressure bar 72 should keep the molten loop material at the desired operating temperature. Typically, a temperature slightly above the melting point of the material is desired. The material is considered to be at or above the "melting point" if the material is partially or wholly in the liquid state. If the loop material is kept at too high a temperature, the loop material may not be viscous enough to form the member 22A which subsequently forms the loop 22 may flow into a small, somewhat semispherically shaped puddle and a loop will not be formed. Conversely, if the temperature of the loop material is too low, the loop material may not transfer from the pressure bar 72 to the doctor blade assembly 74 or print cylinder 60 or, subsequently, may not properly transfer from the print cylinder 60 to the substrate 24 in the desired array or pattern, or the distal end 30 may not fuse with an adjacent loop 22 or back upon itself.

The print cylinder 60 is preferably heated to prevent solidification of the loops 22 during transfer from the heated pressure bar 72 through the deposition on the substrate 24. Generally a print cylinder 60 surface temperature near the source material temperature is desired. A print cylinder 60 temperature of about 178° C. has been found to work well with the polyester hot melt adhesive marketed by the Bostik Company of Middleton, Mass. as No. 7199. But, the operating temperature of the print cylinder 60 may vary according to the particular loop material being used. There are many methods which can be used to heat the print cylinder 60, which will be readily apparent to one skilled in the art. A particularly preferred method of heating the prim cylinder 60 is by using an infrared heater (not shown).

It is to be recognized that a chill roll may be necessary if the substrate 24 is adversely affected by the heat transferred from the loop material. If a chill roll is desired, it may be incorporated into the backing roll 62 using means well known in the art. This arrangement is often necessary if a polypropylene, polyethylene or other polyolefinic substrate 24 is used.

After being deposited onto the substrate 24, the material is severed from the depositing member by a severing means. The material is severed to form the member 22A including the shank 28 and distal end 30 of the female component 20, and a moil. As used herein the term "moil" refers to any material severed from the loop 22 which does not form part of the female component.

The severing means 70 should be adjustable to accommodate various sizes of loops 22 and also provide uniformity throughout the cross-machine direction of the array as will be described in greater detail below. The term "severing means" refers to anything which longitudinally separates the moil from the female component 20. The term "sever" refers to the act of dividing the moil from the member 22A as described above. The severing means 78 should also be clean and should not rust, oxidize or impart corrodents and contaminates (such as moil material) to the loops 22. A suitable severing means is a wire 78 disposed generally parallel to the axis of the cylinder 60 and roll 62 and spaced from the substrate 24 a distance which is greater than the perpendicular distance from the highest elevation of the solidified loop 22 to the substrate 24.

Preferably the wire 70 is electrically heated to prevent build-up of the molten material on the severing means 70, accommodate any cooling of the loops 22 which occurs between the time the loop material leaves the heated pressure bar and severing occurs and to promote lateral stretching of the shank 28. The heating of the severing means 78 should also provide for uniform temperature distribution in the cross-machine direction, so that an array of loops 22 having substantially uniform geometry is produced.

Generally, as the loop material temperature increases a relatively cooler hot wire 78 temperature severing means can be utilized. Also, as the speed of the substrate 24 is decreased, less frequent cooling of the hot wire 78 occurs as each member 22A and moil are severed, making a relatively lower wattage hot wire 78 more feasible at the same temperatures. It is not necessary that the severing means 78 actually contact the member 22A for severing to occur. The member 22 may be severed by the radiant heat emitted from the severing means 78.

For the embodiment described herein a round cross section nickel-chromium wire 70, having a diameter of about 0.64 millimeters (0.025 inches) heated to a temperature of about 343° C. to about 440° C. has been found suitable. It will be apparent that a knife, laser cutting or other severing means 70 may be substituted for the hot wire 78 described above.

It is important that the severing means 78 be disposed at a position which allows stretching of the loop material to occur prior to the loop 22 being severed from the moil. If the severing means 70 is disposed too close to the plane of the substrate 24, the severing means 70 will truncate the shank 28 which will then be too short to form a loop 22.

A hot wire severing means 70 disposed approximately 3.2 millimeters to 8.3 millimeters (0.125 to 0.325 inches), preferably about 5.7 millimeters (0.225 inches) in the machine direction from the nip point 58, approximately 1.4 millimeters to 6.5 millimeters (0.056 to 0.256 inches), preferably about 4.0 millimeters (0.156 inches) radially outward from the backing roll 62 and approximately 13.7 millimeters to approximately 18.6 millimeters (0.534 to 0.734 inches), preferably about 16.1 millimeters (0.634 inches) radially outwardly from the print cylinder 60 is adequately positioned for the process of manufacture disclosed herein.

In operation, the substrate 24 is transported in a first direction relative to the depositing member. More particularly, the substrate 24 is transported through the nip 58, preferentially drawn by a take-up roll (not shown). This provides a clean area of substrate 24 for continuous deposition of loop material and removes the portions of the substrate 24 having the members 22 and subsequently, via transformation loops 22 deposited thereon. The direction generally parallel to the principal direction of transport of the substrate 24 as it passes through the nip 58 is referred to as the "machine direction". The machine direction, as indicated by the arrows 66 in FIG. 5, is generally orthogonal the centerline of the print cylinder 60 and backing roll 62. The direction generally orthogonal to the machine direction and parallel to the plane of the substrate 24 is referred to as the "cross-machine direction".

The substrate 24 may be drawn through the nip 58 at a speed approximately 0% to approximately 10% greater than the surface speed of the cylinder 60 and roll 62. This is done to minimize bunching or puckering of the substrate 24 near the means for severing 78 the member 22A from the means for depositing the loop material on the substrate 24. The substrate 24 is transported through the nip 58 in the first direction at about 3 to about 31 meters per minute (10 to 100 feet per minute).

The angle of the shank 28 formed after severing can be influenced by the rate of transport of the substrate 24 past the nip 70. If the members 22A have a shank angle α more nearly perpendicular to the substrate 24, a slower rate of transport of the substrate 24 in the first direction is preferred. Conversely, if the rate of transport is increased, the angle α of the shank 28 decreases and the distal end 30 having a greater lateral projection 38 will result.

If desired, the substrate 24 may be inclined at any angle α of approximately 35° to approximately 55°, and preferably about 45°, from the plane of the nip 58 towards the backing roll 62 to utilize the viscoelastic nature of the loop material and properly orient the distal end 30 in the "lateral direction", as well as the longitudinal direction, "longitudinal" being defined herein as a direction having a vector component away from the substrate 24, which direction increases the perpendicular distance of the plane of the substrate 24 at the base 26 of the loop, unless otherwise specified to be a direction having a vector component towards such plane of the substrate. This arrangement also provides a greater force to extract the loop material from the apertures 56 and to pull the loop material away from the print cylinder 60. The angle α from the plane of the nip 58 should be increased as a lesser angle of the shank 28 is desired. Also, increasing the angle of deviation from the plane of the nip 58 has a weak, but positive effect to produce the distal end 30 having a greater lateral projection.

After depositing loop material from the apertures 56 onto the substrate 24, the cylinder 60 and roll 62 continue rotation, in the directions indicated by the arrows 66 of FIG. 5. This results in a period of relative displacement between the transported substrate 24 and the apertures 56 during which period (prior to severing) the loop material bridges the substrate 24 and print cylinder 60. As relative displacement continues, the loop material is stretched until severing occurs and the member 22A is separated from the aperture 56 of the print cylinder 60. As used herein the term "stretch" means to increase in linear dimension, at least a portion of which increase becomes substantially permanent for the life of the female component 20.

As discussed above, it is also necessary to sever the loop material from the print cylinder 60 as part of the process which forms the distal end 30. When severed, the member 22A is longitudinally divided into two parts, a distal end 30 which remains with the female component 20 and a moil (not shown) which remains with the print cylinder 60 and may be recycled, as desired. After the filaments are severed from the moil, the female component 20 is allowed to freeze after the distal end 30 contacts the adjacent loop material or fuses with its own base. After solidification of the members 22A, to thereby form the loops 22, the substrate 24 may be wound into a roll for storage as desired.

For the illustrated operation described herein and illustrated in FIG. 6, a print cylinder 60 having an array of about 15 apertures per centimeter (40 apertures per inch) in both the machine direction and cross machine direction, yielding a grid of about 237 apertures per square centimeter (1600 apertures per square inch), is suitable. This grid density may be advantageously used with a print cylinder 60 having a wall thickness of about 0.16 millimeters (0.004 inches) and a diameter of about 20.3 centimeters (8.0 inches), with apertures 56 having a diameter of 0.30 millimeter (0.012 inches). A backing roll 62 having a diameter of about 20.3 centimeters (8.0 inches) and which is vertically registered has been found to work well with the aforementioned print cylinder 60. The rate of transport of the substrate 24 is about 10.7 meters per minute (35 feet per minute).

A nickel-chromium hot wire 78 having a diameter of about 0.6 millimeters (0.025 inches) disposed approximately 5.7 millimeters (0.225 inches) from the nip 58 in the machine direction, approximately 16.1 millimeters (0.634 inches) radially outward from the print cylinder 60 and approximately 4.0 millimeter (0.156 inches) from the backing roll 62 is heated to a temperature of about 430 degrees Celsius. The female component 20 produced by this operation is substantially similar to that illustrated by FIG. 1, which female component 20 may be advantageously incorporated into the illustrative article of use discussed below.

As illustrated in FIGS. 7, 8 and 10, the loops 22 can be formed to have a variety of different shapes by controlling certain manufacturing perimeters such as the print roll geometry, the rotational speed of the print cylinder and backing roll, the hot melt material temperature and the cooling methodology, among others. For example, the loops 22 illustrated in FIG. 7 are formed such that the distal end 30 of one loop 22 fuses with an adjacent loop 22 occurring in the same row 52. To obtain the loops 22, the print cylinder 60 as illustrated in FIG. 5 would be operably rotated at a speed of approximately 44 ft./min. and the backing roll 62 would be operated at a speed of approximately 45 ft./min. The hot melt material as described above ideally would be maintained at a temperature of approximately 350° F. Upon depositing the hot melt material on the supporting substrate, the hot wire 70 severs the hot melt material. The hot wire 70 which preferably has a diameter of approximately 0.016 inches need not contact the hot melt material directly, but need only be in sufficiently close proximity to cause the hot melt material to become severed. By disposing the wire 70 approximately 0.140 inches from the nip and 0.395 inches from the print cylinder and operating the print cylinder and backing roll at the speed set forth above, the wire 70 should consistently sever the hot melt material as described thereby resulting in the formation of the loops 22 illustrated in FIG. 7.

Referring to FIG. 8, the agglomerated loops 22 are formed by utilizing an apparatus similar to the one illustrated in FIG.

5 and slightly alternating the operating conditions of the apparatus. To form the agglomerated loops 22, both the print cylinder 60 and the backing roll 62 are operated at a speed of approximately 45 ft/min., and the hot melt material temperature is maintained at a temperature of approximately 340° F., which is slightly cooler than for the embodiment of FIG. 7. The wire 70 remains 0.140 inches from the nip and 0.395 inches from the print cylinder with a diameter remaining approximately 0.160 inches.

With regard to the embodiment of FIG. 10 which illustrates a plurality of loops 22 formed wherein the distal end 30 fuses back onto the shank 28 or base 26 from which it extends, the operating conditions of the apparatus illustrated in FIG. 5 are again altered slightly. To form the so-called self-fusing loops 22, the print cylinder 60 is operated at a speed of approximately 45 ft./min. while the backing roll 62 is operated at a speed of approximately 44 ft./min. The hot melt material is again preferably maintained at approximately 360° F. The wire 70 which has a diameter of 0.016 inches is still positioned approximately 0.160 inches from the print cylinder 62, however it is positioned approximately 0.435 inches away from the nip.

Additionally, referring back to FIG. 2, it is important to note that both male and female components, 34 and 20, can be formed on the same substrate 24. Thus, to make the fastening system 10 of FIG. 2 which mates with a complementary fastener, the apertures 58 provided on the print cylinder 60 are arranged differently for sections of rows 80 which assist in forming loops than for section of rows 82 which assist in forming hooks as illustrated with reference to FIG. 9. For example, the apertures 58 of row sections 80 which have a diameter of approximately 0.035 inches are typically arranged such that the apertures are disposed in offset linear rows 84 and 84A, respectively, with a distance of approximately 0.044 inches from the center point of two consecutive apertures in any given row as indicated by reference numeral 86. Likewise, the approximate distance between the center points of two adjacent apertures provided in adjacent rows, 84 and 84A, respectively, is also 0.044 inches as indicated by reference numeral 88. Further, the distance between the center points of two adjacent apertures in alternating offset rows 84 and 84A, respectively is only about 0.028 inches as indicated by reference numeral 90.

By way of further example, the apertures 58 of row sections 82 are arranged in staggered and offset rows 92 and 92A, respectively, while the diameter of each aperture 58 remains approximately 0.035 inches. The distance between center points of consecutive apertures in any given row is increased to approximately 0.088 inches as indicated by reference numeral 94. Thus, a gap of approximately 0.044 inches occurs between consecutive apertures in any given row. Additionally, while the distance between the center points of adjacent apertures disposed in adjacent rows remains approximately 0.044 inches in the cross machine direction as indicated by reference numeral 96, the distance between adjacent apertures disposed in adjacent rows is approximately 0.022 inches from their respective center points in the print direction as indicated by reference numeral 98.

With regard to the processing parameters, a fastening system 10 as illustrated in FIG. 2 can be produced utilizing the aperture arrangement of FIG. 9 by operating the print cylinder 60 at approximately 44 ft./min. and the backing roll 62 at approximately 45 ft./min. Ideally, the hot melt material temperature will be maintained at approximately 350° F. with the wire 70 being disposed 0.140 inches from the print cylinder 60 and about 0.395 inches from the nip.

ILLUSTRATIVE ARTICLE OF USE

Figure 11:
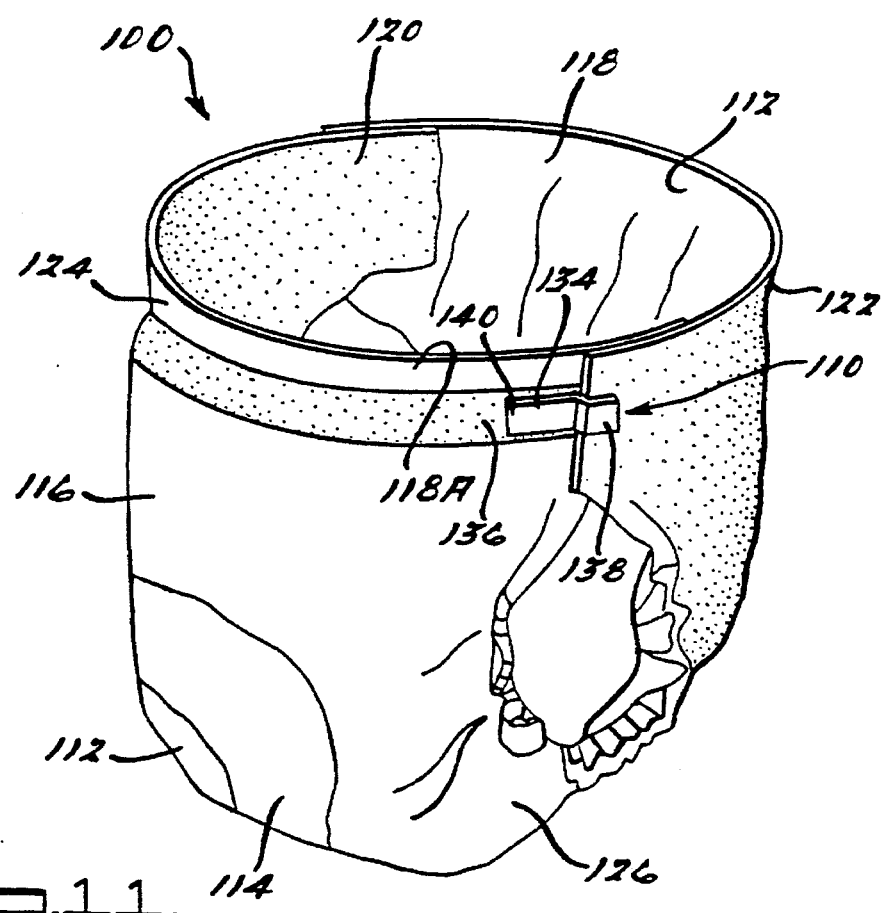
FIG. 11 is a view of a disposable absorbent article utilizing a fastening system of the present invention, showing the topsheet and core partially cutaway.

An illustrative and nonlimiting example of the usage of the fastening system 10 of the present invention in an article of manufacture follows and is illustrated in FIG. 11. Mechanical fastening systems have been advantageously used in disposable absorbent articles as disclosed in U.S. Pat. No. 4,846,815, filed on Dec. 18, 1987, in the name of Scripps, which reference is incorporated herein by reference for the purpose of showing a diaper 100 structure and the advantageous utilization of mechanical fastening systems 10 in such diaper 100 structures.

It is known, for example, that mechanical fastening systems are less easily contaminated by oils and powders than are adhesive tape fastening systems and, further, may be easily reused. All of these features provide advantages when applied to a disposable diaper intended for use on an infant. Also, a refastenable fastening system provides the advantage the infant may be checked to see if soiling of the disposable diaper has occurred during the wearing period.

Referring to FIG. 11, there is shown a disposable diaper 100 intended to be worn about the lower torso by an infant. As used herein, the term "disposable absorbent article" refers to a garment generally worn by infants or incontinent persons and which is drawn between the legs, fastened about the waist of the wearer and intended to be discarded after a single use and not to be laundered or restored. A "disposable diaper" is a particular disposable article intended and scaled to be worn by an infant. Incorporated by reference, some examples of preferred disposable diapers are described in U.S. Pat. Nos. 5,151,092 which issued Sep. 29, 1992, to Buell et al.; 5,242,436 which issued Sep. 7, 1993, to Weil et al.; and 3,860,003 which issued Jan. 14, 1975, to Buell et al., all of which are hereby expressly incorporated by reference.

A preferred diaper 100 comprises a liquid pervious topsheet 112, a liquid impervious backsheet 116, and an absorbent core 114 intermediate the topsheet 112 and backsheet 116. The topsheet 112 and backsheet 116 are at least partially peripherally joined to ensure the core 114 is held in position. The diaper 100 elements may be assembled in a variety of configurations well known to one skilled in the art, with preferred configurations being generally described in U.S. Pat. No. 3,860,003 issued Jan. 14, 1975, to Buell, and U.S. Pat. No. 4,699,622 issued Oct. 13, 1987, to Toussant et al., which patents are incorporated herein by reference for the purpose of disclosing particularly preferred diaper configurations.

The topsheet 112 and backsheet 116 of the diaper 100 are generally coextensive and at least partially peripherally joined together as noted above. Joining of the topsheet 112 and backsheet 116 may be accomplished by a hot-melt adhesive, such as Adhesive No. 1258 manufactured by the H.B. Fuller Company of Vadnais Heights, Minn. The absorbent core 114 has length and width dimensions generally less than that of the topsheet 112 and backsheet 116. The core 114 is interposed between the topsheet 112 and backsheet 116 in a fixed relationship.

The diaper 100 periphery comprises oppositely disposed first and second ends 118 and 118A. The diaper 100 has a first waist portion 122 and a second waist portion 124 extending respectively from the first end 118 and second end 118A of the diaper periphery towards the lateral centerline of the diaper 100 a distance of about one-fifth to about one-third the length of the diaper 100. The waist portions 122 and 124 comprise those portions of the diaper 100 which, when worn, encircle the waist of the wearer and are generally at the highest elevation of the diaper 100 when the wearer is in the standing position. The crotch 126 of the diaper 100 is that portion of the diaper 100 disposed between the first and second waist portions 122 and 124 and which, when worn is positioned between the legs of the wearer.

The absorbent "core" is any means for absorbing and retaining liquid body exudates. The absorbent core 114 is generally compressible, conformable, and nonirritating to the skin of the wearer. A preferred core 114 has first and second opposed faces and may, if desired, be further encased by tissue layers. One opposed face of the core 114 is oriented towards the topsheat 112 and the other opposed face is oriented towards the backsheet 116.

The absorbent core 114 is superimposed on the backsheet 116 and preferably joined thereto by any means well known in the art such as adhesive bonding. In a particularly preferred embodiment, the adhesive bonding which joins the core 114 to the backsheet 116 is accomplished by applying adhesive in the form of a spiral. The backsheet 116 is impervious to liquids and prevents liquids absorbed by and contained in the absorbent core 114 from wetting undergarments, clothing, bedding and any other objects which contact the diaper 100. As used herein, the term "backsheer" refers to any barrier disposed outwardly of the core 114 as the diaper 100 is worn and which contains absorbed liquids within the diaper 100. Preferably, the backsheet 116 is a polyolefinic film of about 0.025 to about 0.030 mm (0.001–0.0012 inches) in thickness. A polyethylene film is particularly preferred, with suitable films being manufactured by Tredegar Industries of Richmond, Va. and the Clopay Corporation of Cincinnati, Ohio. If desired, the backsheet 116 may be embossed or matte finished to provide a more cloth-like appearance or be provided with passages to permit escape of vapors.

The topsheet 112 is compliant, tactilely pleasing and nonirritating to the wearer's skin. The topsheet 112 prevents contact of the absorbent core 114 and liquids therein with the skin of the wearer. The topsheet 112 is liquid pervious, permitting liquids to readily penetrate therethrough. As used herein, the term 'topsheet" refers to any liquid pervious facing which contacts the skin of the wearer while the diaper 100 is being worn and prevents the core 114 from contacting the skin of the wearer. The topsheet 112 may be made of woven, nonwoven, spunbonded or carded materials. A preferred topsheet 112 is a 100% polypropylene nonwoven, carded or spunbonded by means to those skilled in the nonwoven fabrics art. A particularly preferred topsheet 112 has a weight of about 21 to about 24 grams per square meter, a minimum dry tensile strength of about 138 grams per centimeter in the machine direction and a wet tensile strength of at least about 80 grams per centimeter in the cross-machine direction.

The diaper 100 is provided with a fastening system 110 comprising a male component 134 and a female component 136 for maintaining the first waist portion 122 and second waist portion 124 in an overlapping configuration when the diaper 100 is worn, so that the diaper 100 is secured to the wearer. Thus, the diaper 100 is fitted to the wearer and a side closure is formed when the male component 134 is secured to the female component 136.

The fastening system 110 should resist the separation forces which occur during the wearing period. The term "separation forces" refers to forces acting on the fastening system 110 which tend to cause separation, release or removal of the male component 134 from the female component 136. Separation forces include both shear and peel forces. The term "shear force" refers to distributive forces acting generally tangential to the female component 136 and which may be thought of as being generally parallel to the plane of the substrate of the female component 136. The term "peel forces" refers to distributive forces acting in the generally longitudinal direction, and perpendicular to the plane of the female component 136 and male component 134 substrates.

Shear forces are measured by tensile pulling of the male component 134 and female component 136 in opposite directions generally parallel to the planes of the respective substrates. The method used to determine the resistance of a fastening system 110 to shear forces is more fully set forth in U.S. Pat. No. 4,699,622 issued Oct. 13, 1987, to Toussant et al., which patent is incorporated herein by reference.

Peel forces are measured by tensile pulling of the male component 134 from the female component 136 at an included angle of about 135°. The method used to determine the resistance of a fastening system 110 to peel forces is more fully set forth in U.S. Pat. No. 4,846,815 filed Nov. 18, 1987, in the name of Scripps, which reference is incorporated herein by reference.

Separation forces are typically generated by movements of the wearer or by the wearer trying to unfasten the diaper 100. Generally, an infant should not be able to unfasten or remove a diaper 100 the infant is wearing, nor should the diaper 100 come unfastened in the presence of ordinary separation forces which occur during normal wearing. However, an adult should be able to remove the diaper 100 to change it when soiled or check to see if soiling has occurred. Generally, the fastening system 110 should resist a peel force of a least 200 grams, preferably at least about 500 grams, and more preferably, at least about 700 grams. Furthermore, the fastening system 110 should resist a shear force of at least 500 grams, preferably at least about 750 grams, and more preferably at least about 1,000 grams.

The female component 136 may be disposed in a first position anywhere on the diaper 100, so long as the female component 136 engages the male component 134 to maintain he first and second waist portions 122 and 124, respectively, in an overlapping configuration. For example, the female component 136 may be disposed on the outside surface of the second waist portion 124, on the inside surface of the first waist portion 122, or any other position on the diaper 100 on which it is disposed so as to engage with the male component 134. The substrate 24 of the female component 136 may be integral, a discrete element joined to the diaper 100, or a single piece of material that is neither divided or discontinuous with an element of the diaper 100, such as the topsheet 112 or backsheet 116.

While the female component 136 may assume various sizes and shapes, the female component 136 preferably comprises one or more integral patches positioned across the outside surface of the second waist portion 124 to allow for maximum fit adjustment at the waist of the wearer. As illustrated in FIG. 11, the female component 136 is preferably an elongate rectangularly shaped strip integrally secured to the outer surface of the second waist portion 124.

The female component 136 is intended to be engaged the complementary male component 134 to provide a secure fit for the diaper 100. The male component 134 may comprise any of the well known configurations utilized for achieving a side closure on a disposable diaper 100. The male component 134 substrate is joined to the diaper 100 in spaced relationship from the female component 136. As shown on FIG. 11, the male component 134 is preferably disposed on both the first and second longitudinal sides of the diaper 100.

A preferred configuration for the male component 134 minimizes any potential contact between the prongs or hooks of the male component 134 and the skin of the wearer. A preferred male component 134 as illustrated is further described in detail in U.S. Pat. No. 3,848,594 issued Nov. 19, 1974, to Buell. An alternatively preferred male component 134 arrangement is described in detail in U.S. Pat. No. 4,699,622 issued Oct. 13, 1987, to Toussant et al., and still another highly preferred male component arrangement is described in U.S. Pat. No. 5,230,851 which issued to Dennis A. Thomas on Jul. 27, 1993, each of the patents being Incorporated herein by reference for the purpose of illustrating various placements of the male component 134 on the disposable diaper 100. A particularly preferred male component 134 disposition is a single tape tab attached to only one side of the diaper. This type of fastening system arrangement is well known in the disposable diaper art and a non-limiting example of this type of fastening system arrangement is described in U.S. Pat. No. 4,846,815 issued Jul. 11, 1989, to Scripps, which is incorporated herein by reference.

The male component 134 of FIG. 10 has a manufacturer's end 138 and an oppositely disposed user's end 140. The manufacturer's end 138 is joined to the diaper 100, preferably in juxtaposition with the first waist portion 122. The user's end 140 is the free end and is secured to the female component 136 when the diaper 100 is secured to the wearer.

After the diaper 100 is fitted about the waist of the wearer, the user's end 140 of the male component 134 is reasonably secured to the female component 136, and preferably positioned on the second waist portion 124, thereby causing the diaper 100 to encircle the waist of the wearer. The diaper 100 has now effected side closure. The prongs or hooks as shown in FIG. 4 extend from the male component 134 of the user's end 140 so that the prongs or hooks intercept the shanks of the loops contained on the female component 136.

In use, the diaper 100 is applied to the wearer by positioning the first waist portion 122 around the wearer's back and drawing the remainder of the diaper 100 between the legs of the wearer so that the second waist portion 124 is disposed across the front of the wearer. The user's ends 140 of the male component 134 are then secured to the female component 136 on the outside surface of the second waist portion 124 to form a side closure.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making one or more free formed loops useful as a component of a mechanical fastening system including complimentary male hooks, the method comprising the steps of:

providing a depositing member having at least one aperture;

providing a molten thermally sensitive material;

providing a substrate;

removing a discrete amount of said molten thermally sensitive material from said aperture;

depositing said removed molten thermally sensitive material onto said substrate;

stretching a portion of said discrete amount of said molten thermally sensitive material in a direction having a vector component parallel to the plane of the substrate so as to free form a member including a base, a shank and a distal portion;

fusing said distal portion of said free formed members either to another free formed member or back upon itself to form an opening for receiving said male hooks; and solidifying said molten thermally sensitive material of said members to form a loop.

2. The method of claim 1, wherein said depositing member comprises a screen.

3. The method of claim 2, wherein said depositing member comprises a print cylinder.

4. The method of claim 1, wherein said step of depositing said molten thermally sensitive material through said apertures comprises using a doctor blade.

5. The method of claim 3, wherein said print cylinder comprises between about 100 apertures per square centimeter to about 900 apertures per square centimeter.

6. The method of claim 4, wherein said print cylinder comprises between 144 apertures per square centimeter to about 576 apertures per square centimeter.

7. The method of claim 1, wherein said depositing member comprises a porous roll including an internal reservoir.

8. The method of claim 7, wherein the step of depositing said molten thermally sensitive material through said apertures comprises supplying molten thermally sensitive material under pressure to said internal reservoir.

9. The method of claim 1, wherein the step of solidifying said member comprises differentially cooling said molten thermally sensitive material.

10. The method of claim 4, wherein said step of providing a substrate comprises providing a substrate which is transported in a first direction.

\* \* \* \* \*

UNITED STATES PATENT AND TRADEMARK OFFICE
CERTIFICATE OF CORRECTION

PATENT NO. : 5,622,578  
DATED : April 22, 1997  
INVENTOR(S) : Dennis A. Thomas It is certified that error appears in the above-identified patent and that said Letters Patent is hereby corrected as shown below:

Column 1, line 36, "utilizes" should be --utilize--.

Column 1, line 38, "open" should be --often--.

Column 2, line 6, "stow" should be --slow--.

Column 2, line 41, "needled shaped" should be --needle-shaped--.

Column 2, line 49, "deuce" should be --device--.

Column 2, line 61, "led" should be --less--.

Column 3, line 1, "forth" should be --form--.

Column 3, line 66, "mu" should be --will--.

Column 4, line 6, "Is" should be --is--.

Column 4, line 10, "," should be --;--.

Column 4, line 29, "see" should be --self--.

Column 4, line 61, ":" should be --;--.

Column 5, line 5, "composes" should be --comprises--.

Column 5, line 28, "stats" should be --state--.

Column 5, line 29, "book" should be --back--.

UNITED STATES PATENT AND TRADEMARK OFFICE
CERTIFICATE OF CORRECTION

PATENT NO. : 5,622,578
DATED : April 22, 1997
INVENTOR(S) : Dennis A. Thomas

It is certified that error appears in the above-indentified patent and that said Letters Patent is hereby corrected as shown below:

Column 5, line 33, "simple" should be --similar--.

Column 5, line 40, "centerline" should be --centerlines--.

Column 5, line 55, "Z" should be --22--.

Column 5, line 67, "mail" should be --moil--.

Column 6, line 1, "in" should be --is--.

Column 6, line 9, "us" should be --an--.

Column 6, line 11, "hook." should be --hooks--.

Column 6, line 12, "plans" should be --plane--.

Column 6, line 23, "joint" should be --join--.

Column 6, line 57, "continuous" should be --contiguous--.

Column 6, line 59, "me" should be --the--.

Column 7, line 14, "structure" should be --structural--.

Column 7, line 19, "subs" should be --substrate--.

Column 7, line 23, after "loop" insert --22--.

Column 10, line 55, "or" should be --of--.

UNITED STATES PATENT AND TRADEMARK OFFICE
CERTIFICATE OF CORRECTION

PATENT NO. : 5,622,578
DATED : April 22, 1997
INVENTOR(S) : Dennis A. Thomas

It is certified that error appears in the above-indentified patent and that said Letters Patent is hereby corrected as shown below:

Column 11, line 62, "prim" should be --print--.

Column 12, line 16, "moll" should be --moil--.

Column 17, line 22, ""backsheer"" should be --"backsheet"--.

Column 19, line 12, "Incorporated" should be --incorporated--.

Signed and Sealed this

Twenty-third Day of December, 1997

Attest:

BRUCE LEHMAN

Attesting Officer

Commissioner of Patents and Trademarks